US00PP19123P2

(12) United States Plant Patent
Schräder

(10) Patent No.: US PP19,123 P2
(45) Date of Patent: Aug. 19, 2008

(54) ***OSTEOSPERMUM* PLANT NAMED 'SUMOST 03'**

(50) Latin Name: *Osteospermum ecklonis*
Varietal Denomination: Sumost 03

(76) Inventor: Ralf Schräder, Karl-Leisner-Str. 15, D-59348 Lüdinghausen (DE)

( * ) Notice: Subject to any disclaimer, the term of this patent is extended or adjusted under 35 U.S.C. 154(b) by 0 days.

(21) Appl. No.: 11/728,157

(22) Filed: Mar. 23, 2007

(51) Int. Cl.
*A01H 5/00* (2006.01)

(52) U.S. Cl. ..... Plt./360
(58) Field of Classification Search ..... Plt./360
See application file for complete search history.

(56) References Cited

PUBLICATIONS

UPOV–ROM GTITM Computer Database 2007/05 GTI Jouve Retrieval Software Citation for 'Sumost 03'.*

* cited by examiner

*Primary Examiner*—Annette H Para
(74) *Attorney, Agent, or Firm*—C. A. Whealy

(57) ABSTRACT

A new and distinct cultivar of *Osteospermum* plant named 'Sumost 03', characterized by its compact, upright and outwardly spreading plant habit; freely branching growth habit; freely and continuous flowering habit; and daisy-type inflorescences with orange-colored ray florets.

1 Drawing Sheet

Botanical designation: *Osteospermum ecklonis.*
Cultivar denomination: 'Sumost 03'.

BACKGROUND OF THE INVENTION

The present invention relates to a new and distinct cultivar of *Osteospermum* plant, botanically known as *Osteospermum ecklonis,* and hereinafter referred to by the name 'Sumost 03'.

The new *Osteospermum* is a product of a planned breeding program conducted by the Inventor in Lüdinghausen, Germany. The objective of the program is to create and develop new compact *Osteospermum* cultivars with attractive and unique inflorescence coloration.

The new *Osteospermum* originated from a cross-pollination by the Inventor in February, 2002 of a proprietary selection of *Osteospermum ecklonis* identified as code number XY4, not patented, as the female, or seed, parent with a proprietary selection of *Osteospermum ecklonis* identified as code number 01-18, not patented, as the male, or pollen, parent. The new *Osteospermum* was discovered and selected by the Inventor as a single flowering plant within the progeny of the stated cross-pollination in a controlled environment in Lüdinghausen, Germany in May, 2003.

Asexual reproduction of the new *Osteospermum* by terminal cuttings in a controlled environment in Lüdinghausen, Germany since June, 2003, has shown that the unique features of this new *Osteospermum* are stable and reproduced true to type in successive generations.

SUMMARY OF THE INVENTION

The cultivar Sumost 03 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sumost 03'. These characteristics in combination distinguish 'Sumost 03' as a new and distinct cultivar of *Osteospermum:*

1. Compact, upright and outwardly spreading plant habit.
2. Freely branching growth habit.
3. Freely and continuous flowering habit.
4. Daisy-type inflorescences with orange-colored ray florets.

In side-by-side comparisons conducted in Lüdinghausen, Germany, plants of the new *Osteospermum* differ from plants of the female parent selection in the following characteristics:

1. Plants of the new *Osteospermum* are more freely flowering than plants of the female parent selection.
2. Plants of the new *Osteospermum* have smaller inflorescences than plants of the female parent selection.
3. Plants of the new *Osteospermum* and the female parent selection differ in ray floret coloration as plants of the female parent selection have soft orange-colored ray florets.

In side-by-side comparisons conducted in Lüdinghausen, Germany, plants of the new *Osteospermum* differ from plants of the male parent selection in the following characteristics:

1. Plants of the new *Osteospermum* are more compact than plants of the male parent selection.
2. Plants of the new *Osteospermum* and the male parent selection differ in ray floret coloration as plants of the male parent selection have lighter orange-colored ray florets.

Plants of the new *Osteospermum* can be compared to plants of the *Osteospermum* cultivar Sumost 02, disclosed in U.S. Plant Pat. No. 15,975. In side-by-side comparisons conducted in Lüdinghausen, Germany, plants of the new *Osteospermum* differed from plants of the cultivar Sumost 02 in the following characteristics:

1. Plants of the new *Osteospermum* were more compact than plants of the cultivar Sumost 02.
2. Plants of the new *Osteospermum* had shorter internodes than plants of the cultivar Sumost 02.
3. Plants of the new *Osteospermum* had smaller inflorescences than plants of the cultivar Sumost 02.
4. Plants of the new *Osteospermum* and the cultivar Sumost 02 differed in ray floret coloration as plants of the cultivar Sumost 02 had soft orange-colored ray florets.
5. Plants of the new *Osteospermum* did not product seeds whereas plants of the cultivar Sumost 02 produced seeds.

BRIEF DESCRIPTION OF THE PHOTOGRAPH

The accompanying photograph illustrates the overall appearance of the new *Osteospermum*. This photograph shows the colors as true as it is reasonably possible to obtain in colored reproductions of this type. Colors in the photograph may differ slightly from the color values cited in the detailed botanical description which accurately describe the colors of the new *Osteospermum*. The photograph comprises a top perspective view of a typical flowering plant of 'Sumost 03'.

DETAILED BOTANICAL DESCRIPTION

In the following description, color references are made to The Royal Horticultural Society Colour Chart, 2001 Edition, except where general terms of ordinary dictionary significance are used. The aforementioned photograph, following observations and measurements describe plants grown 10.5-cm containers in Lüdinghausen, Germany during the summer and autumn in a glass-covered greenhouse and under conditions and practices which approximate those generally used in commercial *Osteospermum* production. During the production of the plants, day temperatures ranged from 18° C. to 22° C., night averaged 16° C. and light levels ranged from 3,000 to 6,000 kilolux. Measurements and numerical values represent averages for typical flowering plants. Plants were pinched one time and were about four months old when the photograph and description were taken.

Botanical classification: *Osteospermum ecklonis* cultivar Sumost 03.

Parentage:

*Female, or seed, parent.*—Proprietary selection of *Osteospermum ecklonis* identified as code number XY4, not patented.

*Male, or pollen, parent.*—Proprietary selection of *Osteospermum ecklonis* identified as code number 01-18, not patented.

Propagation:

*Type.*—Terminal vegetative cuttings.

*Time to initiate roots, summer.*—About 16 to 20 days at 20° C. to 22° C.

*Time to initiate roots, winter.*—About 14 to 16 days at 16° C. to 18° C.

*Time to produce a rooted cutting, summer.*—About 28 to 30 days at 20° C. to 22° C.

*Time to produce a rooted cutting, winter.*—About 22 to 24 days at 16° C. to 18° C.

*Root description.*—Medium thickness, fleshy; 161D in color.

*Rooting habit.*—Moderate branching; moderately dense.

Plant description:

*Plant form/growth habit.*—Compact, upright and outwardly spreading plant habit. Inflorescences positioned above the foliar plane. Moderately vigorous growth habit.

*Plant height.*—About 25 cm.

*Plant diameter.*—About 15 cm.

*Lateral branches.*—Quantity per plant: Freely branching, about five to six lateral branches per plant. Length: About 25 cm. Diameter: About 3 mm to 4 mm. Internode length: About 0.8 cm to 1 cm. Strength: Strong. Texture: Smooth, glabrous. Color: 144A to 144B.

*Foliage description.*—Arrangement: Alternate, simple; sessile. Length: About 5 cm to 6 cm. Width: About 2.2 cm to 2.5 cm. Shape: Lanceolate. Apex: Acute. Base: Obtuse. Margin: Entire. Texture, upper and lower surfaces: Smooth, glabrous. Venation pattern: Pinnate. Color: Developing foliage, upper surface: 147A. Developing foliage, lower surface: 146A. Fully expanded foliage, upper surface: 146A; venation, 145C. Fully expanded foliage, lower surface: 146A to 146B; venation, 145C.

Inflorescence description:

*Appearance.*—Daisy-type inflorescence form with obovate-shaped ray florets. Inflorescences positioned above the foliage, arising from leaf axils. Disc and ray florets developing acropetally on a capitulum. Inflorescences face mostly upright. Freely flowering habit; about 25 to 30 inflorescences develop over time per plant. Inflorescences not persistent. Inflorescences slightly fragrant, sweet.

*Flowering response.*—In Germany, plants of the new *Osteospermum* flower recurrently to continuously from March to October. Plants begin flowering about 32 to 40 days after pinching. Inflorescences last about six days on the plant.

*Inflorescence bud.*—Height: About 1.3 cm to 1.6 cm. Diameter: About 9 mm. Shape: Ovate. Color: N25B.

*Inflorescence size.*—Diameter: About 4 cm to 4.5 cm. Depth (height): About 1 cm. Disc diameter: About 1 cm to 1.2 cm. Receptacle diameter: About 8 mm. Receptacle height: About 5 mm. Receptacle color: 145C.

*Ray florets.*—Shape: Obovate. Length: About 2 cm. Width: About 4 mm. Apex: Obtuse. Base: Acute. Margin: Entire. Texture: Smooth, glabrous. Number of ray florets per inflorescence: About 26 in a single whorl. Color: When opening, upper surface: N25B. When opening, lower surface: N25A. Fully opened, upper surface: N25B to N25C; towards the base, close to 155D; at the base, N89A; color becoming closer to N25A with development. Fully opened, lower surface: N25B to N25C.

*Disc florets.*—Shape: Tubular; apex dentate, five-pointed. Length: About 4 mm. Diameter: About 1 mm. Number of disc florets per inflorescence: About 70. Color, immature: Apex: 59B. Mid-section and base: 145C. Color, mature: Apex: 59A. Mid-section and base: 145C.

*Phyllaries.*—Quantity per inflorescence: About 20. Length: About 1.2 cm. Width: About 2 mm. Shape: Lanceolate. Apex: Acuminate. Base: Truncate. Margin: Entire. Texture, upper surface: Smooth, glabrous. Texture, lower surface: Pubescent, rough. Color, upper and lower surfaces: Close to 146C.

*Peduncles.*—Length: About 6 cm to 7 cm. Diameter: About 2 mm. Strength: Strong. Aspect: Mostly upright. Texture: Smooth, glabrous. Color: 145A.

*Reproductive organs.*—Androecium: Present on disc florets only. Filament length: About 3 mm. Filament color: 29A. Anther shape: Ovate. Anther length: About 1 mm. Anther color: 59A. Pollen amount: Scarce. Pollen color: 29A. Gynoecium: Present on both ray and disc florets. Pistil length: About 3 mm. Stigma shape: Bi-parted. Stigma color: N89A. Style length: About 2 mm. Style color: Close to 155C.

*Seeds/fruits.*—Seed and fruit development have not been observed.

Disease/pest resistance: Plants of the new *Osteospermum* have not been shown to be resistant to pathogens and pests common to *Osteospermums.*

Temperature tolerance: Plants of the new *Osteospermum* have been observed to tolerate temperatures ranging from about 1° C. to about 40° C.

It is claimed:

1. A new and distinct *Osteospermum* plant named 'Sumost 03' as illustrated and described.

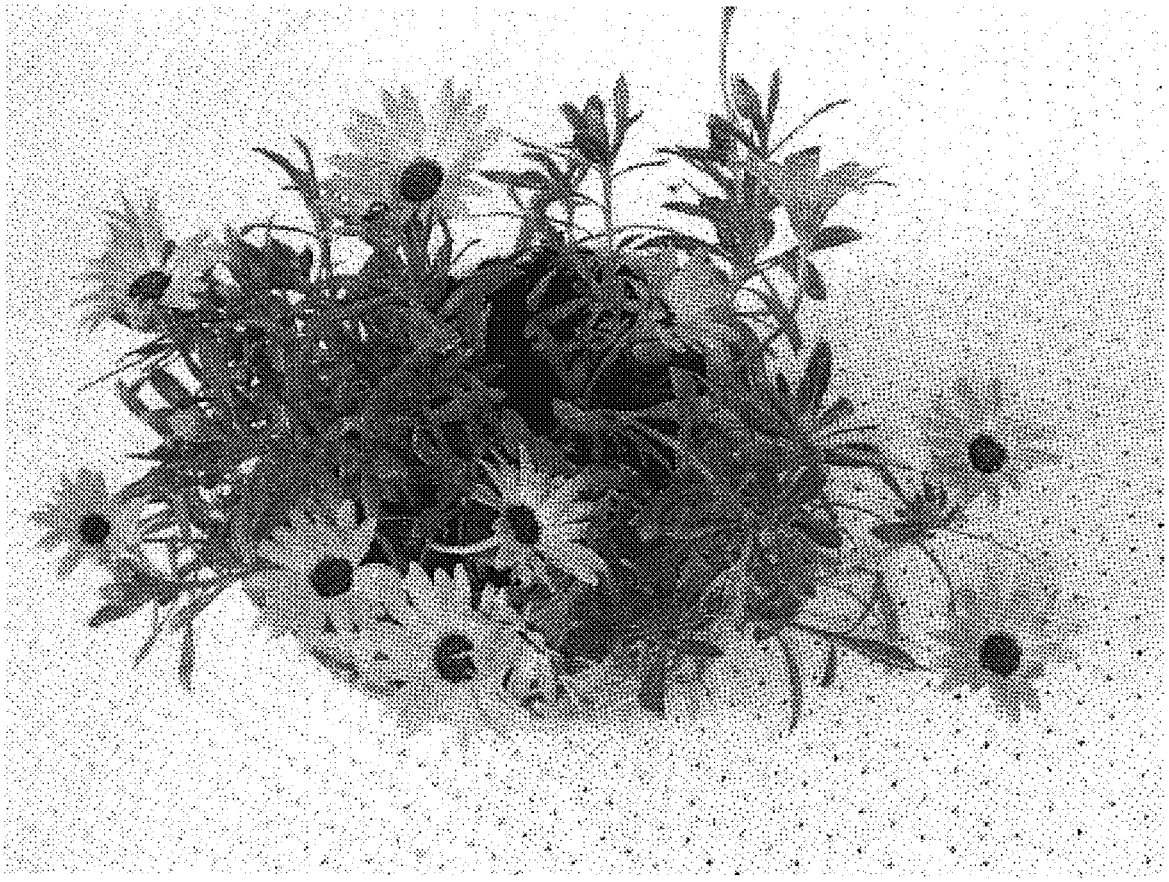

* * * * *